United States Patent [19]

Young et al.

[11] Patent Number: 4,957,932

[45] Date of Patent: Sep. 18, 1990

[54] BENZOHETERAZOLES

[75] Inventors: Robert N. Young, Senneville; Robert Zamboni, Longueuil, both of Canada

[73] Assignee: Merck Frosst Canada, Inc., Kirkland, Canada

[21] Appl. No.: 125,049

[22] Filed: Nov. 25, 1987

[51] Int. Cl.$^5$ .................. C07D 763/56; A61K 31/42
[52] U.S. Cl. .................... 514/375; 546/270; 548/179; 548/180; 548/217; 548/327; 548/330
[58] Field of Search .................... 514/375; 548/217

[56] References Cited

FOREIGN PATENT DOCUMENTS 219436  4/1987  European Pat. Off. .
228959  7/1987  European Pat. Off. .
2190377 11/1987 United Kingdom ............... 514/375

OTHER PUBLICATIONS

C. D. Perchonock et al., J. Med. Chem. 1986, 29, 1442–1452.

*Primary Examiner*—Robert Gerstl
*Attorney, Agent, or Firm*—Gabriel Lopez; Hesna J. Pfeiffer

[57] ABSTRACT

Compounds having the formula:

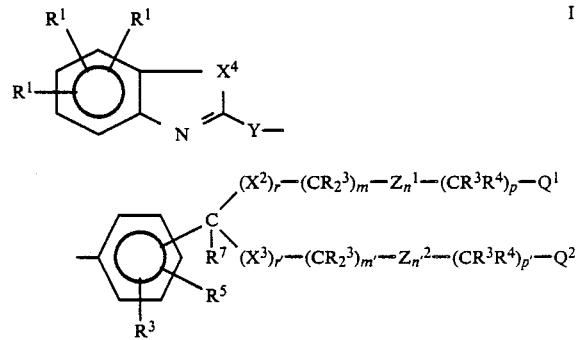

are leukotriene antagonists and inhibitors of leukotriene biosynthesis. These compounds are useful as anti-asthmatic, antiallergic, anti-inflammatory, and cytoprotective agents.

13 Claims, No Drawings

BENZOHETERAZOLES

BACKGROUND OF THE INVENTION

The leukotrienes and their biological activities, especially their roles in various disease states and conditions have been described. For example, see U.S. Pat. No. 4,683,325 (July 28, 1987), which is incorporated herein by reference.

Several classes of compounds exhibit the ability to antagonize the action of leukotrienes in mammals, especially humans. See for example: U.K. Nos. 2,058,785 and 2,094,301; and EP Nos. 56,172, 61,800 and 68,739.

EP No. 110,405 (June 13, 1984) describes anti-inflammatory and antiallergic substituted benzenes which are disclosed to be leukotriene inhibitors, i.e., inhibitors of the 5-lipoxygenase pathway.

SUMMARY OF THE INVENTION

The present invention relates to compounds having activity as leukotriene and SRS-A antagonists or inhibitors of the biosynthesis of the leukotrienes, to methods for their preparation, to intermediates useful in their preparation and to methods and pharmaceutical formulations for using these compounds in mammals (especially humans).

Because of their activity as leukotriene antagonists or biosynthetic inhibitors, the compounds of the present invention are useful as anti-asthmatic, anti-allergic, and anti inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemic; noxious agent induced damage or necrosis of hepatic, pancreatic, renal, or nyocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compounds of this invention are best realized by Formula I:

$R^1$ is H, halogen, $C_1$-$C_8$ alkyl, $C_2$-$C_8$ alkenyl, $C_2$-$C_8$ alkynyl, $-CF_3$, $-SR^2$, $-S(O)R^2$, $-S(O)_2R^2$, $-NR^3R^3$, $-OR^3$, $-COOR^3$, $-(C=O)R^3$, $-C(OH)R^3R^3$, $-CN$, $-NO_2$, $-N_3$, substituted or unsubstituted phenyl, substituted or unsubstituted 2-phenethyl, or substituted or unsubstituted pyridyl;

$R^2$ is $C_1$-$C_8$ alkyl, $C_2$-$C_8$ alkenyl, $C_2$-$C_8$ alkynyl, $-CF_3$, substituted or unsubstituted phenyl, substituted or unsubstituted benzyl, or substituted or unsubstituted 2-phenethyl;

$R^3$ is H or $R^2$;

$R^4$ is H, halogen, $NO_2$, $-CN$, $-OR^3$, $-SR^3$, or $C_1$-$C_8$ alkyl;

$CR^3R^4$ may be the radical of a naturally occurring amino acid;

$R^5$ is H, halogen, $-NO_2$, $-N_3$, $-CN$, $-SR^2$, $-NR^3R^3$, $-OR^3$, $C_1$-$C_8$ alkyl, or $-(C=O)R^3$;

$R^6$ is $-(CH_2)_s-C(R^7R^7)-(CH_2)_s-R^8$ or $R^7$ is H or $C_1$-$C_4$ alkyl;

$R^8$ is
(A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
(B) the radical $W-R^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is $-SR^{11}$, $-OR^{12}$, or $-NR^{12}R^{12}$;

$R^{11}$ is $C_1$-$C_6$ alkyl, $-(C=O)R^{14}$, unsubstituted phenyl, or unsubstituted benzyl;

$R^{12}$ is H, $R^{11}$, or two $R^{12}$ groups joined to the same N may form a ring of 5 or 6 members containing up to two heteroatoms chosen from O, S or N;

$R^{13}$ is $C_1$-$C_8$ alkyl, $C_2$-$C_8$ alkenyl, $C_2$-$C_8$ alkynyl, $-CF_3$, or unsubstituted phenyl, benzyl, or 2-phenethyl;

$R^{14}$ is H or $R^{13}$;

$R^{15}$ is $R^3$ or halogen;

$R^{16}$ is H, $C_1$-$C_4$ alkyl, or OH;

m and m' are independently 0-8;

n and n' are independently 0 or 1;

p and p' are independently 0-8;

m+n+p is 1-10 when $X^2$ is O, S, S(O), or $S(O)_2$;

m+n+p is 0-10 when $X^2$ is $CR^3R^{16}$;

m'+n'+p' is 1-10 when $X^3$ is O, S, S(O), or $S(O)_2$;

m'+n'+p' is 0-10 when $X^3$ is $CR^3R^{16}$;

r is 0 or 1 when $Z^1$ is HET ($-R^3,-R^5$);

r is 1 when $Z^1$ is $-CONR^3$;

r' is 0 or 1 when $Z^2$ is HET($-R^3, -R^5$);

r' is 1 when $Z^2$ is $CONR^3$;

s is 0-3;

$Q^1$ and $Q^2$ are independently $-COOR^3$, tetrazole, $-COOR^6$, $-CONHS(O)_2R^{13}$, $-CN$,

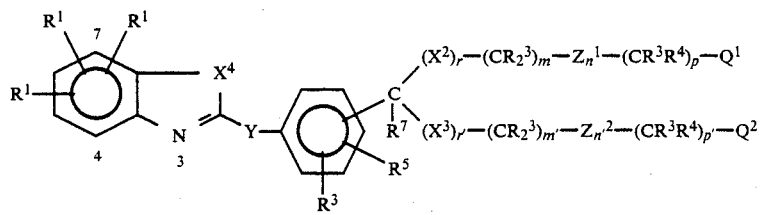

wherein:

$-CONR^{12}R^{12}$, $-CHO$, $-CH_2OH$, $-COCH_2OH$,

—NHS(O)$_2$R$^{13}$; or if Q$^1$ or Q$^2$ is COOH and R$^4$ is —OH, —SH, or —NHR$^3$ then Q$^1$ or Q$^2$ and R$^4$ and the carbons through which they are attached may form a heterocyclic ring by loss of water;

W is O, S, or NR$^3$;

X$^1$ is O, S, —S(O)—, —S(O)$_2$—, —NR$^3$, or —CR$^3$R$^3$—;

X$^2$ and X$^3$ are independently O, S, S(O), S(O)$_2$, or CR$^3$R$^{16}$;

X$^4$ is NR$^3$, O, or S;

Y is —CR$^3$=CR$^3$—, —C≡C—, —CR$^3$R$^3$—X$^1$—, —X$^1$—CR$^3$R$^3$—, —CR$^3$R$^3$—X$^1$—CR$^3$R$^3$—,

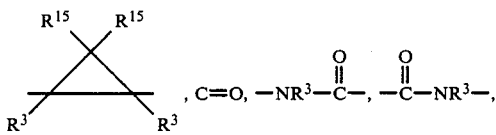

, C=O, —NR$^3$—C—, —C—NR$^3$—,
             ‖         ‖
             O         O

Z$^1$ and Z$^2$ are independently —CONR$^3$— or —HET-(—R$^3$, —R$^5$)—;

HET is

and the pharmaceutically acceptable salts thereof.

Alkyl, alkenyl, and alkynyl are intended to include linear, branched, and cyclic structures and combinations thereof.

As used herein, the term "alkyl" includes "loweralkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-ethyl-2,2-methyl-4-propylnonyl, cyclododecyl, adamantyl, and the like.

As used herein, the term "loweralkyl" includes those alkyl groups of from 1 to 7 carbon atoms. Examples of loweralkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

Alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

As used herein, the term "alkoxy" includes those alkoxy groups of from 1 to 3 carbon atoms of either a straight, branched, or cyclic configuration Examples of alkoxy groups include methoxy, ethoxy, propoxy, isopropoxy, cyclopropyloxy, and the like.

Substituted phenyl, benzyl, and 2-phenethyl, and pyridyl include 1 or 2 substituents on the aromatic ring selected from C$_1$-C$_6$ alkyl, R$^{10}$, NO$_2$, SCF$_3$, —COR$^7$, —COR$^{10}$, CN, halogen, and CF$_3$.

Halogen includes F, Cl, Br and I.

The prodrug esters of Q (i.e., when Q=—COOR$^6$) are intended to include the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3, 451–454 (1987).

When Q and R$^4$ and the carbons through which they are attached form a ring, the rings thus formed include lactones, lactams, and thiolactones.

It is intended that the definitions of any substituent (e.g., R$^1$, R$^2$, m, Q, X, etc.) in a particular molecule be independent of its definitions elsewhere in the molecule. Thus, —NR$^3$R$^3$ represents —NHH, —NHCH$_3$, —NHC$_6$H$_5$, etc.

The heterocycles formed when two groups join through N include pyrrolidine, piperidine, morpholine, thiamorpholine, piperazine, and N-methylpiperazine.

The naturally occurring amino acids, the radicals of which may be CR$^3$R$^4$, include alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine.

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Preferred compounds of Formula I are those wherein:

R$^1$ is H, halogen, C$_1$-C$_8$ alkyl, —CF$_3$, —SR$^2$, —S(O)R$^2$, —S(O)$_2$R$^2$, —OR$^3$, or —CN;

R$^2$ is C$_1$-C$_8$ alkyl or —CF$_3$;

R$^3$ is H or R$_2$;

R$^4$ is H, —OR$^3$, —SR$^3$, NR$^3$R$^3$, or C$_1$-C$_8$ alkyl;

CR$^3$R$^4$ may be the radical of a naturally occurring amino acid;

R$^5$ is H, halogen, —CN, —SR$^2$, —OR$^3$, C$_1$-C$_8$ alkyl, or —(C=O)R$^3$;

R$^6$ is —(CH$_2$)$_s$—C(R$^7$R$^7$)—(CH$_2$)$_s$—R$^8$ or —CH$_2$CONR$^{12}$R$^{12}$;

R$^7$ is H or C$_1$-C$_4$ alkyl;

R$^8$ is
(A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
(B) the radical W-R$^9$;

R$^9$ contains up to 21 carbon atoms and is (1) a hydrocarbon radical or (2) an acyl radical of an organic acyclic or monocyclic carboxylic acid containing not more than 1 heteroatom in the ring;

R$^{10}$ is —SR$^{11}$, —OR$^{12}$, or —NR$^{12}$R$^{12}$;

R$^{11}$ is C$_1$-C$_6$ alkyl, —(C=O)R$^{14}$, unsubstituted phenyl, or unsubstituted benzyl;

R$^{12}$ is H, R$^{11}$, or two R$^{12}$ groups joined to the same N may form a ring of 5 or 6 members containing up to two heteroatoms chosen from O, S or N;

R$^{13}$ is C$_1$-C$_8$ alkyl, —CF$_3$, or unsubstituted phenyl, benzyl, or 2-phenethyl;

R$^{14}$ is H or R$^{13}$;

R$^{15}$ is R$^3$ or halogen;

R$^{16}$ is H, C$_1$-C$_4$ alkyl, or OH;

m and m' are independently 0–4;

n and n' are independently 0 or 1;

p and p' are independently 0–4;

m+n+p is 1–10 when X$^2$ is O or S;

m+n+p is 0–10 when X$^2$ is CR$^6$R$^{16}$;

$m'+n'+p'$ is 1–10 when $X^3$ is O or S;
$m'+n'+p'$ is 0–10 when $X^3$ is $CR^3R^{16}$;
r is 0 or 1 when $Z^1$ is HET ($-R^3$, $-R^5$);
r is 1 when $Z^1$ is $-CONR^3$;
r' is 0 or 1 when $Z^2$ is HET($-R^3$, $-R^5$);
r' is 1 when $Z^2$ is $CONR^3$;
s is 0–3;
$Q^1$ and $Q^2$ are independently $-COOR^3$, tetrazole, $-COOR^6$, $-CONHS(O)_2R^{13}$, $-CONR^{12}R^{12}$, $-NHS(O)_2R^{13}$; or if $Q^1$ or $Q^2$ is COOH and $R^4$ is $-OH$, $-SH$, or $-NHR^3$ then $Q^1$ or $Q^2$ and $R^4$ and the carbons through which they are attached may form a heterocyclic ring by loss of water;
W is O, S, or NH;
$X^1$ is O, S, $-NR^3$, or $CR^3R^{16}$;
$X^2$ and $X^3$ are independently O, S, or $CR^3R^{16}$;
$X^4$ is $-NR^3$, O, or S;
Y is $-CR^3=CR^3-$, $-C\equiv C-$, $-CR^3R^3-X^1-$, or $-X^1-CR^3R^3-$;
$Z^1$ and $Z^2$ are independently $-CONR^3-$ or $-HET-(-R^3, R^5)-$;
HET is

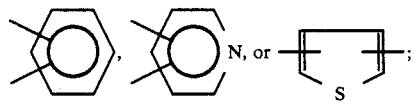

and the pharmaceutically acceptable salts thereof.

It will be understood that in the discussion of methods of treatment which follows, references to the compounds of Formula I are meant to also include the pharmaceutically acceptable salts and the lactone, lactam, and thiolactone forms.

The compounds of Formula I are active as antagonists of SRS A and especially of leukotriene $D_4$. These compounds also have modest inhibitory activity on leukotriene biosynthesis but are primarily of therapeutic interest as antagonists. The activity of the compounds of Formula I can be detected and evaluated by methods known in the art. See for example, Kadin, U.S. Pat. No. 4,296,129.

The ability of the compounds of Formula I to antagonize the effects of the leukotrienes and to inhibit the biosynthesis of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. They are also effective in the treatment of inflammatory diseases of the eye.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are: (A) an ethanol-induced lesion assay and (B) an indomethacin-induced ulcer assay and are described in U.S. Pat. No. 4,683,325 (July 28, 1987).

The leukotriene antagonist properties of compounds of the present invention were evaluated using the following assays.

Guinea Pig Ileum Preparation for Evaluation of Antagonists of Leukotriene $D_4$ and Other Mediators Tissue:

Sections of ileum were taken from male Hartley strain guinea pigs (Charles River, U.S.A.) 300 to 500 g which were sacrificed by a blow to the head and exsanguinated. Terminal ileum was removed, cleaned with warm Tyrode's solution and then divided into segments of approximately 1.5–2.0 cm each. The segments of ileum were then mounted under 1 g tension in a 20 ml organ bath containing 10 ml of Tyrode's solution with the following composition (mM): NaCl, 137; KCl, 2.7; $MgSO_4 \cdot 7H_2O$, 0.8; $CaCl_2$, 1.8; $NaH_2PO_4$, 0.42; $NaHCO_3$, 11.9; Dextrose, 5.6. The bathing solution was continuously aerated with 95% $O_2$ and 5% $CO_2$ and bath temperature was maintained at 37° C. The beta-adrenoceptor blocker, timolol (0.5 μg/ml) and the antimuscarinic agent atropine (1.0 μM) were present in the Tyrode's solution. Isometric tension changes were recorded using Grass FT03 force displacement transducers (Grass Instrument G., Quincy, Mass.) connected to a Beckman Type R Dynograph. The output (analog) signals from all channels of the Beckman Dynograph were converted to digital signals (DL-12 Data Logger, Buxco Electronics). These signals were subsequently fed into an IBM-XT computer for storage and subsequent analysis (Buxco Electronics Custom Software). In order to wash tissue, the bath solution was automatically aspirated and replaced with a constant volume (10 ml) of fresh solution by means of timer controlled solenoid valves.

Antagonist Testing:

After the tissues were stable, a standard dose of 0.3 ng/ml $LTD_4$ (100 μl) was repeatedly added (timer controlled Harvard Pump) to the bath every 4.5 minutes (1 minute contact, 30 second wash, 3 minute rest) until a consistent response was obtained (minimum of 4 responses). Addition of $LTD_4$ was performed automatically with two 4-channel Harvard Apparatus Syringe Pumps which delivered 100 μl (final bath concentration 0.3 ng/ml) of agonist simultaneously to all tissues every 4.5 minutes. Following each addition of $LTD_4$ the tissue was washed with Tyrode's solution until baseline tension was re established. After consistent responses were obtained the tissues were used to screen compounds.

Usually, 10 μl of a 10 mg/ml solution of the compound to be tested was added to the bath 30 seconds prior to the addition of $LTD_4$. The compound and $LTD_4$ remained in contact with the tissue until the maximum tension was developed (1 minute) after which the tissue was washed repeatedly until the baseline was re-established. Percent inhibition relative to the immediately preceding control response was computed on an IBM-XT for each dose of test compound (Buxco Electronics Custom Software). If the compound was active (greater than 50% inhibition) then tests were performed with 10 fold serial dilutions until inhibition was less than 50%. Provided the response was inhibited by less than 20%, the tissue was used immediately to evaluate another compound. When the response was inhibited by greater than 20%, cycles of $LTD_4$ alone were added until a consistent response was re-established.

In order to determine the specificity of the active compounds, they were tested against contractions induced by a standard dose of histamine (50 ng/ml) using a similar protocol to that described above (½ minute contact time, 30 seconds wash and 2 minutes rest).

LTD$_4$ Binding:

The results for LTD$_4$ binding were determined by the method of S. S. Pong and R. N. DeHaven, Proc. Nat. Acad. Sci. U.S.A., 80, 7415–7419 (1983).

Compounds of Formula I were tested using the following assay to determine their mammalian leukotriene biosynthesis inhibiting activity.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15–24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/ml. A 500 µl aliquot of PMN suspension and test compound are preincubated for 2 minutes at 37° C., followed by the addition of 10 µM A-23187. The suspension is stirred for an additional 4 minutes then bioassayed for LTB$_4$ content by adding an aliquot to a second 500 µl portion of the PMN at 37° C. The LTB$_4$ produced in the first incubation causes aggregation of the second PMN, which is measured as a change in light transmission. The size of the assay aliquot is chosen to give a submaximal transmission change (usually 70%) for the untreated control. The percentage inhibition of LTB$_4$ formation is calculated from the ratio of transmission change in the sample to the transmission change in the compound-free control.

The following assays can be used to evaluate compounds which are either leukotriene antagonists or inhibitors of leukotriene biosynthesis, or which possess a combination of these two properties.

Antigen Challenge 'in vitro' Assay

Male guinea pigs weighing 300–350 g are sensitized by injecting (intraperitoneally) 0.5 ml of a suspension containing 0.4 mg of egg albumin (Ovalbumin, Grade V, Sigma Chemical Co.) and 4.0 g aluminum hydroxide in 19.6 ml of saline. Two weeks are permitted for sensitization to occur.

Three sensitized guinea pigs are stunned and exanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No. 7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine ($7\times10^{-6}$ M), atropine ($1\times10^{-7}$ M), and indomethacin ($1.4\times10^{-6}$ M) are added to the buffer to block the response to released histamine, acetylcholine, and cyclooxygenase products. To record responses, one end of the tracheal chain is attached to a Gould-Statham UC-2 force displacement transducer which is connected to a Beckman Type R-dynograph. The preparations are allowed to equilibrate for one hour during which time the tissues are automatically washed (10 ml volume displacement) every 6 minutes.

[1]modified Krebs solution in grams/liter and (mM): NaCl - 6.87 (120); glucose - 2.1 (11); NaHCO$_3$ - 2.1 (25); KCl - 0.32 (4.72); CaCl$_2$ - 0.28 (2.5); MgSO$_4$·7H$_2$O - 0.11 (0.5); KH$_2$PO$_4$ - 0.16 (1.2); pH at bathing solution=7.35 ±0.05.

After the equilibration period the tissues are primed with methacholine (10 µg/ml), washed, and allowed to recover to baseline. The tissues are treated again with a second dose of methacholine, washed, allowed to return to baseline and washed for an additional hour.

Two chains are used as a control. These are incubated in a concentration of egg albumin sufficient to induce an average contraction of 50–80% of the methacholine response.

Each compound to be tested is added (at a final bath concentration of 10 µg/ml) 20 minutes prior to challenging the tissue with egg albumin.

The response of the challenged tissue is expressed as a percentage of the methacholine maximum. The percentage inhibition for each compound is then calculated. Compounds which at 10 µg/ml (final concentration) inhibit the egg albumin response by 50% or more are retested at a lower concentration.

Asthmatic Rat Assay

Rats are obtained from an inbred line of asthmatic rats. Both female (190–250 g) and male (260 to 400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. They are used between days 12 and 14 postsensitization. In order to eliminate the serotonin component of the response, rats are pretreated intravenously 5 minutes prior to aerosol challenge with 3.0 µg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes' prior to challenge. They are either dissolved in saline or 1% methocel or suspended in 1% methocel. The volume injected is 1 ml/kg (intravenously) or 10 ml/kg (orally). Prior to oral treatment rats are starved overnight. Their activity is determined in terms of their ability to decrease the duration of symptoms of dyspnea in comparison with a group of vehicle treated controls. Usually, a compound is evaluated at a series of doses and an $ED_{50}$ is determined. This is defined as the dose (mg/kg) which would inhibit the duration of symptoms by 50%.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti asthmatic, anti allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non steroidal antiinflammatory drug (NSAID) that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg, preferably from about 1 mg/kg to about 100 mg/kg. The dosage may be administered in single or divided individual doses.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts derived from inorganic bases include aluminum, ammonium, calcium, copper, ferric, ferrous, lithium, magnesium, manganic, manganous, potassium, sodium, zinc salts and the like. Particularly preferred are the ammonium, calcium, magnesium, potassium, and sodium salts. Salts derived from pharmaceutically acceptable organic non toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric and p-toluenesulfonic acid, and the like. Particularly preferred are hydrobromic, hydrochloric, phosphoric, and sulfuric acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

Dosage forms include tablets, troches, dispersions, suspensions, solutions, capsules, creams, ointments, aerosols, and the like.

For use where a composition for intravenous administration is employed, a suitable dosage range for anti-asthmatic, anti inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti allergic use is, e.g. from about 0.01 mg to about 100 mg of a compound of Formula I per kg of body weight per day, preferably from about 0.1 mg to about 10 mg per kg and for cytoprotective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser, or as a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of Compound I include transdermal devices, aerosols, creams, ointments, lotions, dusting powders, and the like.

For the treatment of diseases of the eye, ophthalmic preparations for ocular administration comprising 0.001-1% by weight solutions or suspensions of the compounds of Formula I in an acceptable ophthalmic formulation may be used.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of | 1 ml |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof. NSAIDs which are within the scope of this invention are those disclosed in U.S. Pat. No. 4,683,325 (July 28, 1987).

Pharmaceutical compositions comprising the Formula I compounds may also contain inhibitors of the biosynthesis of the leukotrienes such as are disclosed in U.S. Pat. No. 4,666,907 (Apr. 19, 1987), U.S. Pat. No. 4,663,307 (May 5, 1987), U.S. Pat. No. 4,611,056 (Sept. 9, 1986), and U.S. Pat. No. 4,634,766 (Jan. 6, 1987), which are hereby incorporated herein by reference.

The compounds of the Formula I may also be used in combination with leukotriene antagonists such as those disclosed in EP No. 106,565 (Apr. 25, 1984) and EP No. 104,885 (Apr. 4, 1984) which are hereby incorporated herein by reference and others known in the art such as those disclosed in EP No. 56,172 (July 21, 1982) and U.S. Pat. No. 4,424,231 (Jan. 3, 1984); and in U.K. Patent Specification No. 2,058,785, which are hereby incorporated herein by reference.

Pharmaceutical compositions comprising the Formula I compounds may also contain as the second active ingredient prostaglandin including thromboxane antagonists such as those disclosed in U.S. Pat. No.

4,536,507 (Aug. 20, 1985), U.S. Pat. No. 4,237,160 (Dec. 2, 1980), EP No. 166,591 (Jan. 2, 1986), and EP No. 234,708 (Sept. 2, 1987). They may also contain histidine decarboxylase inhibitors such as α-fluoro-methyl-histidine, described in U.S. Pa. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP No. 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Another useful pharmaceutical composition comprises the Formula I compounds in combination with serotonin antagonists such as methysergide, the serotonin antagonists disclosed in *Nature*, vol. 316, pages 126–131, 1985, and the like. Each of the references referred to in this paragraph is hereby incorporated herein by reference.

When the second active ingredient in compositions of this invention is a thromboxane synthetase inhibitor, such inhibitor can be as described in UK No. 2,038,821 (e.g., UK-37248 and dazoxiben hydrochloride), U.S. Pat. No. 4,217,357 (e.g., UK-34787), U.S. Pat. No. 4,444,775 (e.g., CGS 13080), U.S. Pat. No. 4,226,878 (e.g., ONO 046), U.S. Pat. No. 4,495,357 (e.g., U635-57A), U.S. Pat. No. 4,273,782 (e.g., UK-38485), or EP No. 98,690 (e.g., CV-4151).

The combination compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration. These compositions are formulated similarly to the compositions discussed above.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following compounds (formula I') are within the scope of the invention:

TABLE 1

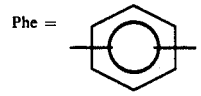

| EXAMPLE | $R^1$ | $X^4$ | Y | $R^5$ | A | B |
|---|---|---|---|---|---|---|
| 1 | 5-Cl | O | CH=CH | H | $SCH_2CH_2CO_2H$ | $SCH_2CH_2CO_2H$ |
| 2 | H | O | CH=CH | H | $SCH_2CH_2CO_2H$ | $SCH_2CH_2CO_2H$ |
| 3 | 6-Br | S | CH=CH | H | $SCH_2CH_2CO_2H$ | $SCH_2CH_2CO_2H$ |
| 4 | 5-Cl | NH | CH=CH | 6-$OCH_3$ | $SCH_2CH_2CO_2H$ | $SCH_2CH_2CO_2H$ |
| 5 | 5-F | O | CH=CH | 5-CN | $SCH_2CH_2CO_2H$ | 3-($CO_2H$)-Phe |
| 6 | 4-$CF_3$ | O | CH=CH | H | $SCH_2CH_2CO_2H$ | 3-($CO_2H$)-5-($COCH_3$)Phe |
| 7 | 4-$SO_2CH_3$ | O | CH=CH | H | $SCH_2CH_2CO_2H$ | $CH_2CH_2$-2-($CO_2H$)Phe |
| 8 | 7-Cl | S | CH=CH | H | $SCH_2CH_2CON(CH_3)_2$ | 3-($CO_2H$)-Phe |
| 9 | H | N—$CH_3$ | CH=CH | H | $SCH_2CH_2CO_2H$ | 3-($CO_2H$)-Phe |
| 10 | H | S | $CH_2O$ | 4-$SCF_3$ | $SCH_2CH_2CO_2H$ | $SCH_2CH_2CO_2H$ |
| 11 | H | S | $CH_2O$ | 6-$C_2H_5$ | $SCH_2CH_2CO_2H$ | 2-($CO_2H$)-Phe |
| 12 | H | S | $CH_2CH_2$ | 6-$COCH_3$ | $SCH_2CH_2CO_2H$ | 2-($CO_2H$)—Phe |
| 13 | H | S | C≡C | H | $SCH_2CH_2CO_2H$ | $SCH_2CH_2CO_2H$ |

Phe = ⌬

Compounds of the present invention can be prepared according to the following methods. Temperatures are in degrees Celsius.

METHOD A

Aniline derivative II is treated with acetic acid and a suitable dehydrating agent such as $P_2O_5/CH_3SO_3H$ to afford adduct III. Derivative III is then transformed to adduct IV (where Z=a leaving group such as halogen) using a suitable reagent such as N-bromosuccinimide (NBS) in the presence of light. Halogen derivative IV is treated with $Ph_3P$ in a solvent such as $CH_3CN$ with heat, if necessary, to form Wittig reagent V.

Isophthaldehyde derivative of structure VI is reacted with an alkanoic acid or tetrazole substituted with a thiol or hydroxy group in an inert solvent such as benzene in the presence of a suitable catalyst such as $BF_3 \cdot OEt_2$ or trimethylsilyl chloride to afford derivative VII.

Wittig reagent V is reacted with a base such as butyl lithium and the aldehyde VII to produce adduct VIII, a representative of structure I.

METHOD B

Aldehyde IX is reacted with an alkanoic acid or tetrazole substituted with a thiol or hydroxy group in an inert solvent such as benzene in the presence of a suitable catalyst such as $BF_3 \cdot OEt_2$ or TMSCl to afford acetal derivative X. Acetal derivative X is then reacted with a derivative of general structure IV, in which Z is a leaving group such as a Br in the presence of a suitable base such as NaOH, NaH, or $K_2CO_3$ in an inert solvent such as THF, dioxane, DMF, etc, with warming, if necessary, to provide adduct XI, a representative of structure I.

METHOD C

Benzoheterazole derivative III is treated with derivative VIa in the presence of a suitable catalyst like $ZnCl_2$ at a temperature above 120° to give adduct XII. Bromoacid derivative XIII is treated first with 2 eq. of base such as BuLi in a suitable solvent such as THF at −100°, then at −78° with III to afford alcohol XIII. Alcohol XIII is reacted with thiol XIV in the presence of a suitable catalyst such as $BF_3$ or $AlCl_3$ to give adduct XV.

METHOD D

Alternatively, adduct XIII can be transformed to XVI where W is a suitable leaving group such as Cl using reaction conditions such as $CCl_4$/trioctylphosphine. XVI is reacted with thiol XIV in the presence of a suitable base such as $K_2CO_3$ to give adduct XV.

METHOD E

Referring to Method E, derivative IV is reacted with a compound of formula IX in the presence of a suitable base such as NaOH, NaH, $K_2CO_3$ or NaOMe in an inert solvent such as THF with warming, if necessary, to provide the adduct XIIa. Using the reactions described in Methods C or D adduct XIIa is transformed to XVII.

METHOD F

Referring to Method F, bromo derivative XVIII can be treated with $Ph_3P$ in a suitable solvent such as toluene or $CH_3CN$ with warming, if necessary, to provide phosphonium salt XIX. The phosphonium salt XIX is first treated with n-butyllithium then with lactol XX to afford styrene adduct XXI. Alcohol XXI is transformed to ester XXII using conventional methods such as $CrO_3$/pyridine followed by $MnO_2$/NaCN/AcOH. Styrene adduct XXII is condensed with thiol XIV is the presence of a suitable catalyst such as $AlCl_3$ to give thiol ether XXIII.

When A=CN, XXIII is converted to the aldehyde XXIV using a suitable reagent such as $SnCl_2$/HCl. The phosphonium salt V is first treated with n-butyl lithium then with XXIV to give benzoheterazole XXV.

When A=OMe, XXIII is demethylated using a suitable reagent such as $BBr_3$ or $AlCl_3$/HSEt to give phenol derivative XXVI. Phenol XXVI is condensed with heterazole derivative IV using a suitable catalyst such as $K_2CO_3$ to afford adduct XXVII.

METHOD G

Referring to Method G, heterazole derivative III is first treated with LDA and then with bromo derivative XVIIIa to afford adduct XXVIII. Cyano derivative XXVIII is reduced to aldehyde XXIX with a reagent such as $SnCl_2HCl$. Using the methodology described in Method C or D XXIX is converted to XXX.

The groups $Q^1$ and $Q^2$ may be modified by hydrolysis of an ester group, removal of a blocking group, or conversion of a nitrile to an amide or tetrazole by heating with tributyltin azide, thus providing additional examples of the leukotriene antagonists of the present invention.

In the following schema Az represents

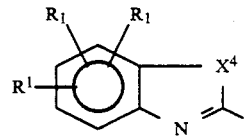

METHOD A

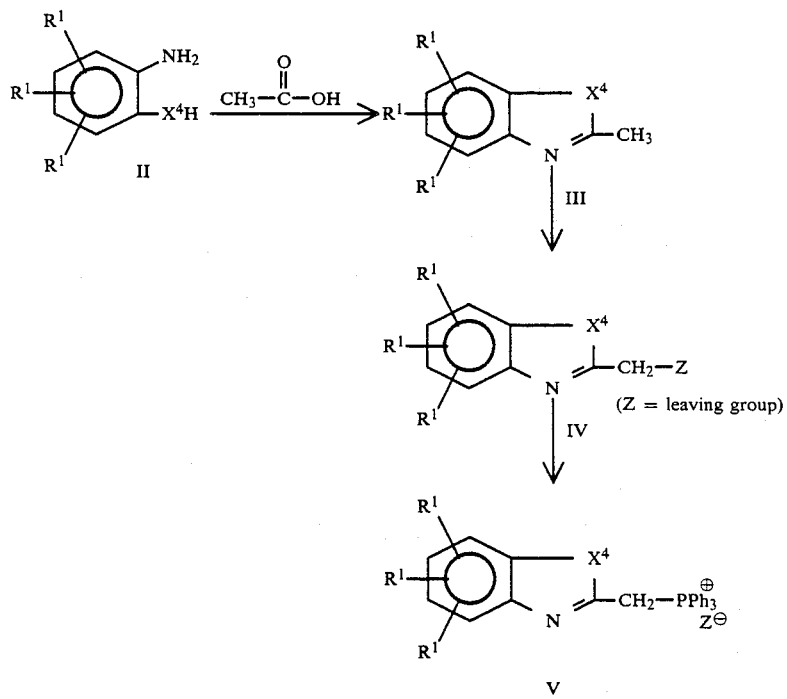

-continued
METHOD A
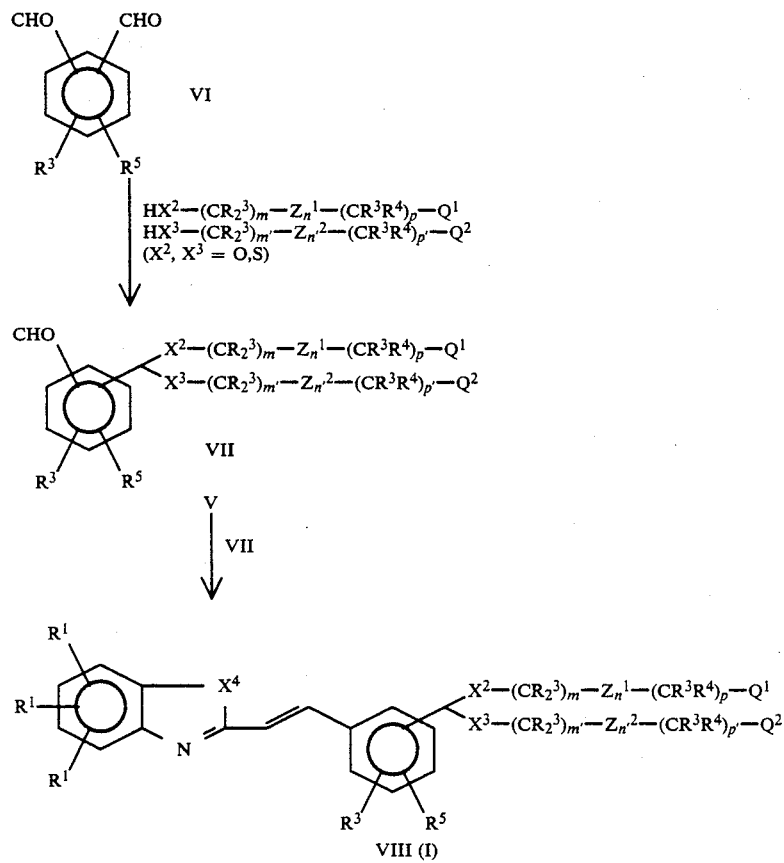
METHOD B
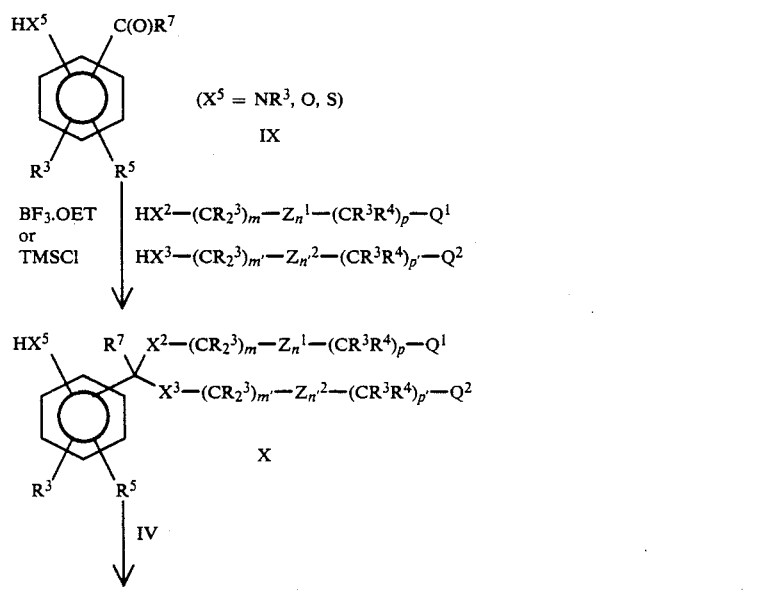

METHOD B
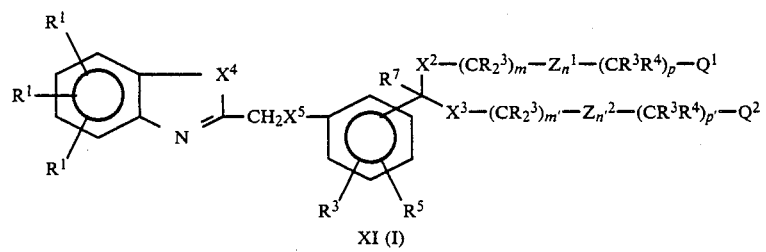
METHOD C
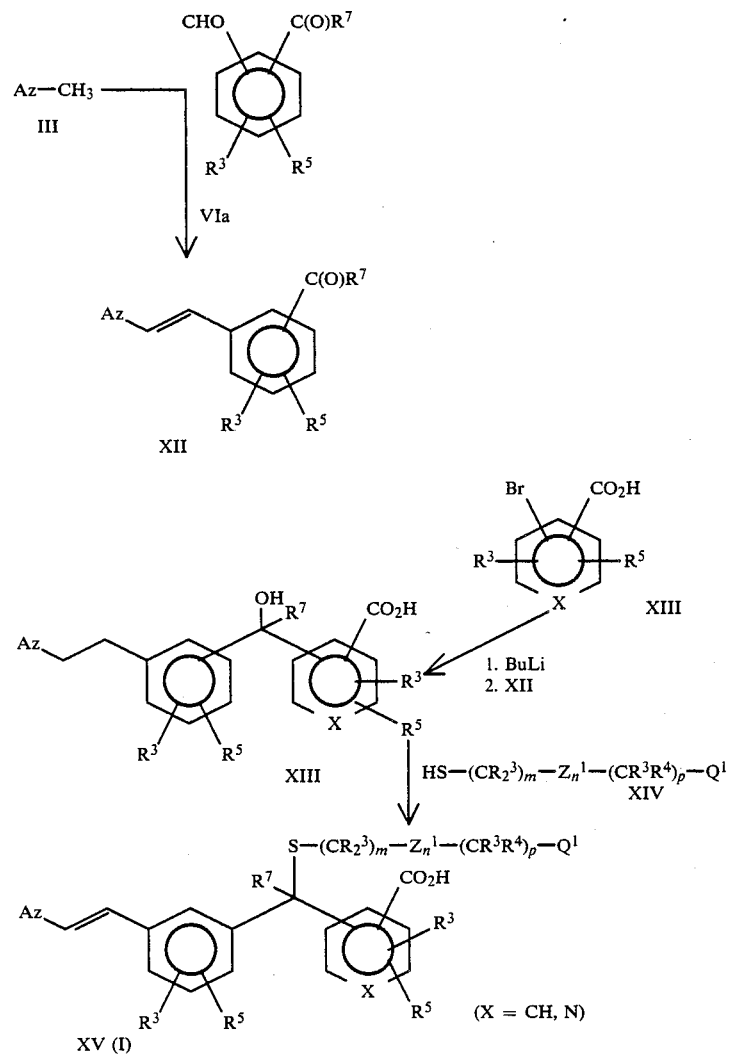
METHOD D
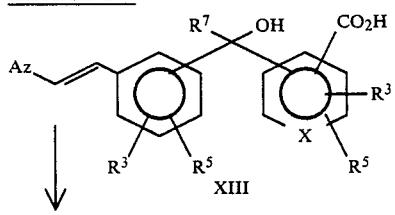
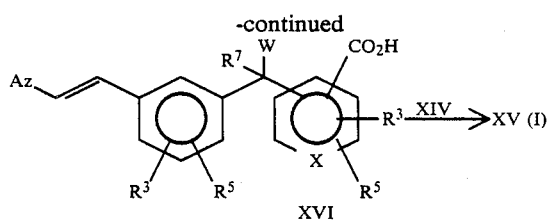

-continued
METHOD E
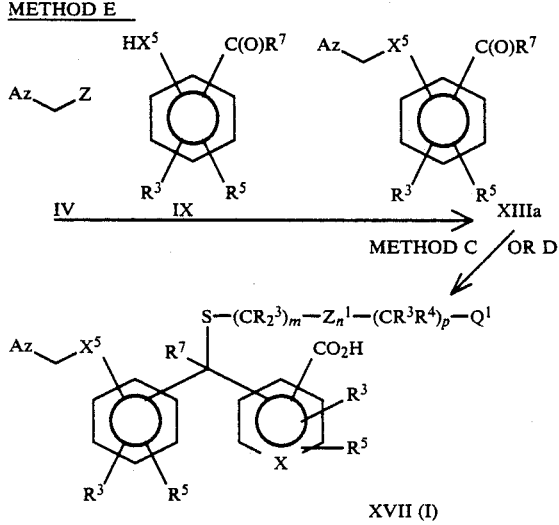
METHOD F
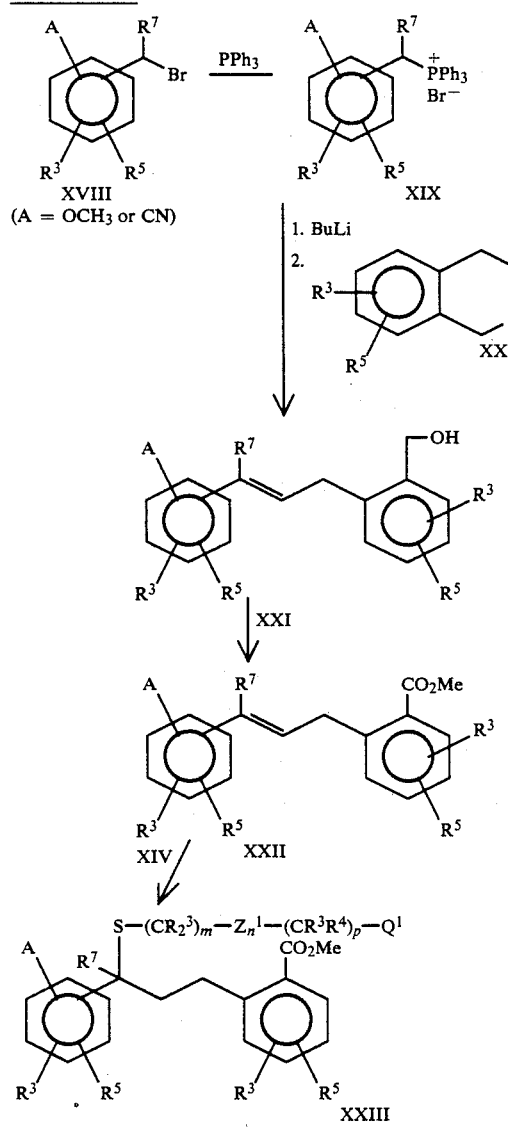
-continued
METHOD F
XXIII (A = CN)
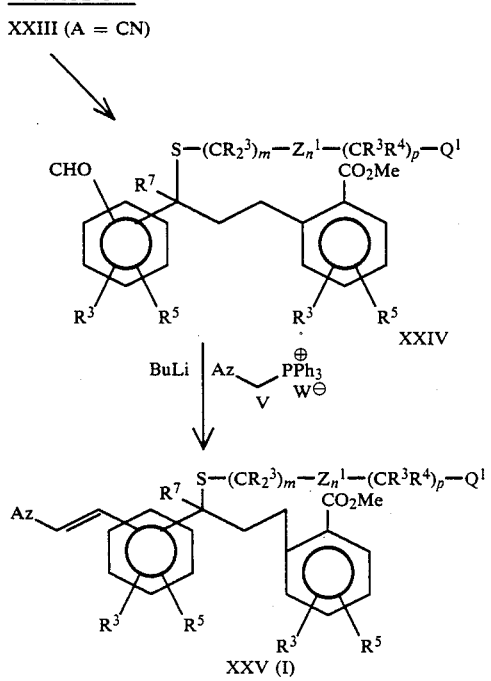
METHOD G
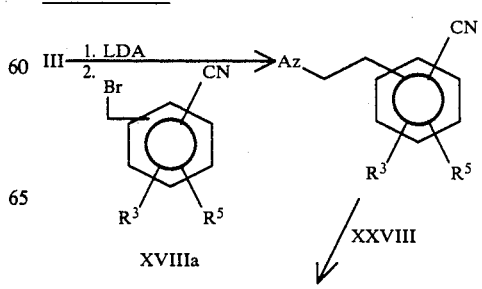

METHOD G

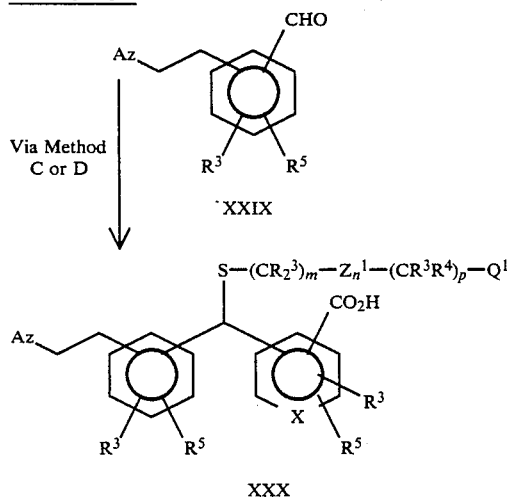

Via Method C or D

The invention is further defined by reference to the following examples, which are intended to be illustrative and not limiting.

All temperatures are in degrees celsius.

EXAMPLE 1

5-(3-(2-(5-chlorobenzoxazol-2-yl)ethenyl))phenyl)-4,6-dithianonanedioc acid

Step 1:

Preparation of dimethyl 5-(3-formylphenyl)-4,6-dithianonanedioate

To a solution of isophthalaldehyde (5.4 g) in $CHCl_3$ (50 mL) and methyl 3-mercaptopropionate (9.2 mL) was added dropwise trimethylsilylchloride (6.5 mL). The reaction mixture was stirred 1 hour at room temperature, quenched with aqueous $NH_4OAc$ (25%), and extracted with ethyl acetate. Flash chromatography of the residue using 1:1 ethyl acetate/ hexane afforded the title compound.

p.m.r. ($CD_3COCD_3$) δ(ppm): 2.6-3.0 (m, 8H); 3.60 (s, 6H); 5.4 (s, 1H); 7.6 (t, 1H); 7.8-8.0 (m, 2H); 8.05 (m, 1H); 10.05 (s, 1H).

Step 2

Preparation of 5-chloro-2-methylbenzoxazole

To a solution of $P_2O_5$ (1 g) and methanesulphonic acid (10 g) was added 2-amino-5-chlorophenol (1.6 g) and glacial acetic acid (570 μL). The reaction mixture was stirred at 70° C. overnight and then at 90° for 4 hours. The mixture was poured into a well stirred saturated aqueous $NaHCO_3$ solution (200 mL) and extracted with EtOAc (3x). The organic extracts were dried and evaporated. Purification of the residue by column chromatography using toluene/EtOAc (10:0.2) as eluant afforded the title compound as a pink solid.

p.m.r. ($CDCl_3$) δ(ppm): 2.65 (s, 3H), 7.25 (dd, 1H), 7.4 (d, 1H), 7.65 (d, 1H).

Step 3

Preparation of 5-chloro-2-bromomethyl-benzoxazole

A solution of the benzoxazole (1.3 g) (Step 2) in $CCl_4$ (15 mL) was treated with N-bromo-succinimide (NBS) (1.5 g) and benzoyl peroxide (38 mg) at reflux using a U.V. lamp for 24 hours. Filtration, evaporation, and flash chromatography of the residue using 1:1 hexane/toluene afforded the title compound which was used as such for the next step.

Step 4

Preparation of (5 chlorobenzoxazol-2-yl methyl)triphenylphosphonium bromide

A solution of the bromide (500 mg) (Step 3) and triphenylphosphine (740 mg) in $CH_3CN$ (5 mL) was stirred at room temperature overnight. The reaction mixture was diluted with $Et_2O$ (20 mL), stirred for 30 min, and filtered to give the title compound as a white solid.

Step 5

Dimethyl 5-(3-(2-(5-chlorobenzoxazol-2-yl )ethenyl)phenyl)-4,6-dithianonanedioate To a solution of phosphonium bromide (780 mg) (Step 4) in tetrahydrofuran (THF) (8 mL) at −78° was added dropwise 1 eq. of n-BuLi in hexane. The solution was stirred at −78° for 15 min. Then (545 mg) of the aldehyde (Step 1) in THF (4 mL) was added dropwise and the reaction mixture was stirred at −78° for 1 hour. The reaction mixture was poured into pH 7 buffer, extracted with ethyl acetate, dried and evaporated. The residue was chromatographed on a column of $SiO_2$ using 10:1 toluene/ethyl acetate to afford the title compound, m.p. 66°-67° C.

p.m.r. ($CDCl_3$) δ(ppm): 2.5-2.7 (m, 4H), 2.75-3.0 (m, 4H), 3.7 (s, 6H), 5.05 (s, 1H), 7.05 (d, 1H), 7.25-7.6 (m, 5H), 7.7 (bs, 2H), 7.8 (d, 1H).

Step 6

To a solution of diester (Step 5) (400 mg) in dimethylforamide (DMF) (10 mL) was added 2 N LiOH (1.6 mL). The reaction mixture was stirred at room temperature for 3.5 hours. The mixture was then diluted with $H_2O$ (100 mL) and extracted with ethyl acetate. The aqueous phase was acidified with 1 N HCl and extracted with ethyl acetate. The organic extracts were dried and evaporated. Flash chromatography of the residue using $CH_2Cl_2$/acetone/AcOH (10:2:0.05) as eluant afforded the title compound, m.p. 160°-164°.

Anal. calc'd for $C_{22}H_{20}ClNO_5S_2 \cdot 0.5H_2O$: C 54.26; H 4.35; N 2.88; S 13.17; Cl 7.28. Found C 54.55; H 4.35; N 2.65; S 13.76; Cl 7.42.

What is claimed is:

1. A compound of the formula:

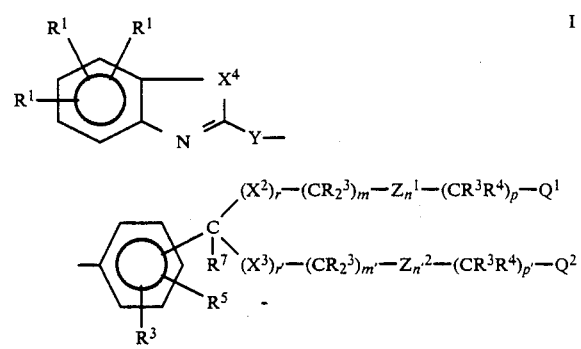

wherein:

$R^1$ is H, halogen, $C_1$-$C_8$ alkyl, $C_2$-$C_8$ alkenyl, $C_2$-$C_8$ alkynyl, $-CF_3$, $-SR^2$, $-S(O)R^2$, $-S(O)_2R^2$, $-NR^3R^3$, $-OR^3$, $-COOR^3$, $-(C=O)R^3$, $-C(OH)R^3R^3$, $-CN$, $-NO_2$, $-N_3$, substituted or unsubstituted phenyl, substituted or unsubstituted benzyl, substituted or unsubstituted 2-phenethyl, or substituted or unsubstituted pyridyl;

$R^2$ is $C_1-C_8$ alkyl, $C_1-C_8$ alkenyl, $C_2-C_8$ alkynyl, —$CF_3$, substituted or unsubstituted phenyl, substituted or unsubstituted benzyl, or substituted or unsubstituted 2-phenethyl;

$R^3$ is H or $R^2$;

$R^4$ is H, halogen, —$NO_2$, —CN, —$OR^3$, —$SR^3$, $NR^3R^3$, or $C_1-C_8$ alkyl;

$R^5$ is H, halogen, —$NO_2$, —$N_3$, —CN, —$SR^2$, —$NR^3R^3$, —$OR^3$, $C_1-C_8$ alkyl, or —(C=O)$R^3$;

$R^6$ is —$(CH_2)_s$—$C(R^7R^7)$—$(CH_2)_s$—$R^8$ or —$CH_2CONR^{12}R^{12}$;

$R^7$ is H or $C_1-C_4$ alkyl;

$R^8$ is
(A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
(B) the radical W-$R^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is —$SR^{11}$, —$OR^{12}$, or —$NR^{12}R^{12}$;

$R^{11}$ is $C_1-C_6$ alkyl, —(C=O)$R^{14}$, unsubstituted phenyl, or unsubstituted benzyl;

$R^{12}$ is H, $R^{11}$, or two $R^{12}$ groups joined to the same N may form a ring of 5 or 6 members containing up to two heteroatoms chosen from O, S or N;

$R^{13}$ is $C_1-C_8$ alkyl, $C_2-C_8$ alkenyl, $C_2-C_8$ alkynyl, —$CF_3$, or unsubstituted phenyl, benzyl, or 2-phenethyl;

$R^{14}$ is H or $R^{13}$;

$R^{15}$ is $R^3$ halogen;

$R^{16}$ is H, $C_1-C_4$ alkyl, or OH;

m and m' are independently 0-8;

n and n' are independently 0 or 1;
p and p' are independently 0-8;
m+n+p is 1-10 when $X^2$ is O, S, S(O), or S(O)$_2$;
m+n+p is 0-10 when $X^2$ is $CR^3R^{16}$;
m'+n'+p' is 1-10 when $X^3$ is O, S, S(O), or S(O)$_2$;
m'+n'+p' is 0-10 when $X^3$ is $CR^3R^{16}$;
r is 0 or 1 when $Z^1$ is HET (—$R^3$, —$R^5$);
r is 1 when $Z^1$ is $CONR^3$;
r' is 0 or 1 when $Z^2$ is HET(—$R^{3,}$—$R^5$);
r' is 1 when $Z^2$ is $CONR^3$;
s is 0-3;
$Q^1$ and $Q^2$ are independently —$COOR^3$, tetrazole, —$COOR^6$, —$CONHS(O)_2R^{13}$, —CN, —$CONR^{12}R^{12}$, —CHO, —$CH_2OH$, —$COCH_2OH$, —$NHS(O)_2R^{13}$; or if $Q^1$ or $Q^2$ is COOH and $R^4$ is —OH, —SH, or —$NHR^3$ then $Q^1$ or $Q^2$ and $R^4$ and the carbons through which they are attached may form a heterocyclic ring by loss of water;

W is O, S, or —$NR^3$;
$X^1$ is O, S, —S(O)—, —S(O)$_2$—, —$NR^3$, or —$CR^3R^3$—;
$X^2$ and $X^3$ are independently O, S, S(O), S(O)$_2$, or $CR^3R^{16}$;
$X^4$ is O;
Y is —$CR^3$=$CR^3$—, —C≡C—, —$CR^3R^3$—$X^1$—, —$X^1$—$CR^3R^3$—, —$CR^3R^3$—$X^1$—$CR^3R^3$—,

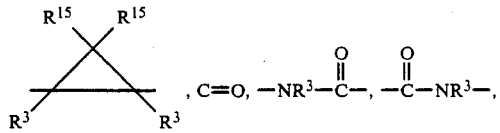, C=O, —$NR^3$—$\overset{O}{\underset{\|}{C}}$—, —$\overset{O}{\underset{\|}{C}}$—$NR^3$—, O, S, or $NR^3$;

$Z^1$ and $Z^2$ are independently —$CONR^3$— or —HET(—$R^3$, —$R^5$)—;
HET is

substituted phenyl, benzyl, 2-phenethyl, and pyridyl mean 1 or 2 substituents on the aromatic ring selected from $C_1-C_6$ alkyl, $R^{10}$, $NO_2$, $SCF_3$, —$COR^7$, —$COR^{10}$, CN, halogen, and $CF_3$;

and the pharmaceutically acceptable salts thereof.

2. A compound of claim 1 of Formula I' wherein the substituents are as follows:

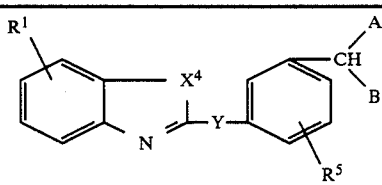

| $R^1$ | $X^4$ | Y | $R^5$ | A | B |
|---|---|---|---|---|---|
| 5-Cl | O | CH=CH | H | $SCH_2CH_2CO_2H$ | $SCH_2CH_2CO_2H$ |
| H | O | CH=CH | H | $SCH_2CH_2CO_2H$ | $SCH_2CH_2CO_2H$ |
| 5-F | O | CH=CH | 5-CN | $SCH_2CH_2CO_2H$ | 3-($CO_2H$)-Phe |
| 4-$CF_3$ | O | CH=CH | H | $SCH_2CH_2CO_2H$ | 3-($CO_2H$)-5-($COCH_3$)Phe |
| 4-$SO_2CH_3$ | O | CH=CH | H | $SCH_2CH_2CO_2H$ | $CH_2CH_2$-2-($CO_2H$)Phe |

3. The following compound of claim 2: 5-(3-(2-(5-chlorobenzoxazol-2-yl)ethenyl))phenyl)-4,6-dithianonanedioc acid.

4. A compound of claim 1 wherein:
$R^1$ is H, halogen $C_1-C_8$ alkyl, —$CF_3$, —$SR^2$, —S(O)$R^2$, —S(O)$_2R^2$, —$OR^3$, or —CN;
$R^2$ is $C_1-C_8$ alkyl or —$CF_3$;
$R^3$ is H or $R^2$;
$R^4$ is H, —$OR^3$, —$SR^3$, —$NR^3R^3$, or $C_1-C_8$ alkyl;
$CR^3R^4$ may be the radical of a naturally occurring amino acid;
$R^5$ is H, halogen, —CN, —$SR^2$, —$OR^3$, $C_1-C_8$ alkyl, or —(C=O)$R^3$;

$R^6$ is —(CH$_2$)$_s$—C(R$^7$R$^7$)—(CH$_2$)$_s$—R$^8$ or —CH$_2$CONR$^{12}$R$^{12}$;

$R^7$ is H or C$_1$-C$_4$ alkyl;

$R^8$ is
(A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
(B) the radical W-R$^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is —SR$^{11}$, —OR$^{12}$, or —NR$^{12}$R$^{12}$;

$R^{11}$ is C$_1$-C$_6$ alkyl, —(C=O)R$^{14}$, unsubstituted phenyl, or unsubstituted benzyl;

$R^{12}$ is H, R$^{11}$, or two R$^{12}$ groups joined to the same N may form a ring of 5 or 6 members containing up to two heteroatoms chosen from O, S or N;

$R^{13}$ is C alkyl, —CF$_3$, or unsubstituted phenyl, benzyl, or 2-phenethyl;

$R^{14}$ is H or R$^{13}$;

$R^{15}$ is R$^3$ or halogen;

$R^{16}$ is H, C$_1$-C$_4$ alkyl, or OH;

m and m' are independently 0–4;

n and n' are independently 0 or 1;

p and p' are independently 0–4;

m+n+p is 1–10 when X$^2$ is O or S;

m+n+p is 0–10 when X$^2$ is CR$^3$R$^{16}$;

m'+n'+p' is 1–10 when X$^3$ is O or S;

m'+n'+p' is 0–10 when X$^3$ is CR$^3$R$^{16}$;

r is 0 or 1 when Z$^1$ HET (—R$^3$, —R$^5$);

r is 1 when Z$^1$ is —CONR$^3$;

r' is 0 or 1 when Z$^2$ is HET(—R$^3$, —R$^5$);

r' is 1 when Z$^2$ CONR$^3$;

s is 0–3;

$Q^1$ and $Q^2$ are independently —COOR$^3$, tetrazole, —COOR$^6$, —CONHS(O)$_2$R$^{13}$, —CONR$^{12}$R$^{12}$, —NHS(O)$_2$R$^{13}$; or if Q$^1$ or Q$^2$ is COOH and R$^4$ is —OH, —SH, or —NHR$^3$ then Q$^1$ or Q$^2$ and R$^4$ and the carbons through which they are attached may form a heterocyclic ring by loss of water;

W is O, S, or NH;

$X^1$ is O, S, —NR$^3$, or —CR$^3$R$^3$—;

$X^2$ and $X^3$ are independently O, S, or CR$^3$R$^{16}$;

Y is —CR$^3$=CR$^3$—, —C≡C—, —CR$^3$R$^3$—X$^1$—, or —X$^1$—CR$^3$R$^3$—;

$Z^1$ and $Z^2$ are independently —CONR$^3$— or —HET(—R$^3$, —R$^5$)—;

HET is

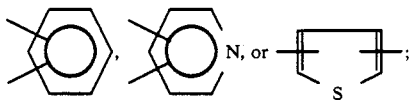

and the pharmaceutically acceptable salts thereof.

5. A pharmaceuticall composition for preventing the synthesis, the action, or the release of SRS-A or leukotrienes in a mammal comprising a therapeutically effective amount of a compound of claim 1 and a pharmaceutically acceptable carrier.

6. The pharmaceutical composition of claim 5 additionally comprising an effective amount of a second active ingredient selected from the group consisting of non-steroidal anti inflammatory drugs; peripheral analgesic agents; cyclooxygenase inhibitors; leukotriene antagonists; leukotriene bisynthesis inhibitors; H$_2$-receptor antagonists; antihistaminic agents; prostaglandin antagonists; thromboxane antagonists; thromboxane synthetase inhibitors; and ACE antagonists.

7. A pharmaceutical composition according to claim 6, wherein the second active ingredient is a non-steroidal anti-inflammatory drug.

8. A pharmaceutical composition of claim 7, wherein the weight ratio of said compound of claim 1 to said second active ingredient ranges from about 1000:1 to 1:1000.

9. A method of preventing the synthesis, the action, or the release of SRS-A or leukotrienes in a mammal which comprises administering to said mammal an effective amount of a compound of claim 1.

10. The method of claim 9 wherein the mammal is man.

11. A method of inducing cytoprotection in a mammal comprising administering to a mammal in need of such treatment a cytoprotective amount of a compound of claim 1.

12. A method of treating inflammatory diseases of the eye in a mammal which comprises administering to a mammal in need of such treatment a therapeutically effective amount of a compound of claim 1.

13. The method of claim 12 wherein the mammal is man.

* * * * *